United States Patent
Hetz et al.

(10) Patent No.: US 10,545,201 B2
(45) Date of Patent: Jan. 28, 2020

(54) DEVICE AND METHOD FOR POSITIONING IN A MAGNETIC FIELD OF A MAGNETIC RESONANCE TOMOGRAPHY SYSTEM USING MAGNETIC FIELD STRENGTH

(71) Applicants: Christian Hetz, Pretzfeld (DE); Markus Petsch, Erlangen (DE); Ronny Pflichtbeil, Fürth (DE); Rolf Schmidt, Immenreuth (DE); Johann Sukkau, Herzogenaurach (DE)

(72) Inventors: Christian Hetz, Pretzfeld (DE); Markus Petsch, Erlangen (DE); Ronny Pflichtbeil, Fürth (DE); Rolf Schmidt, Immenreuth (DE); Johann Sukkau, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 48 days.

(21) Appl. No.: 15/892,824

(22) Filed: Feb. 9, 2018

(65) Prior Publication Data
US 2018/0231622 A1 Aug. 16, 2018

(30) Foreign Application Priority Data
Feb. 15, 2017 (DE) .................. 10 2017 202 399

(51) Int. Cl.
*G01R 33/30* (2006.01)
*G01R 33/00* (2006.01)
(Continued)

(52) U.S. Cl.
CPC ....... *G01R 33/307* (2013.01); *G01R 33/0023* (2013.01); *G01R 33/072* (2013.01); *G01R 33/543* (2013.01)

(58) Field of Classification Search
CPC G01R 33/307; G01R 33/0023; G01R 33/072; G01R 33/543; A61B 5/0555
See application file for complete search history.

(56) References Cited

U.S. PATENT DOCUMENTS 8,390,290 B2 * 3/2013 Sukkau .............. G01R 33/3415
324/318
8,415,949 B2 * 4/2013 Biber .................. G01R 33/341
324/307
(Continued)

FOREIGN PATENT DOCUMENTS

DE 102009021026 A1 11/2010
DE 102016203255 A1 8/2017

OTHER PUBLICATIONS

German Office Action for German Application No. 102017202399.6, dated Oct. 26, 2017.

*Primary Examiner* — G. M. A Hyder
(74) *Attorney, Agent, or Firm* — Lempia Summerfield Katz LLC

(57) ABSTRACT

The disclosure relates to a positioning device for positioning in a static magnetic field of a magnetic resonance tomography system and a magnetic resonance tomography system. The positioning device may be moved along a first axis in the magnetic field. Herein, the positioning device includes a plurality of magnetic-field-strength sensors arranged at a distance from one another in the direction of the first axis in predetermined positions on the positioning device.

15 Claims, 4 Drawing Sheets

(51) Int. Cl.
*G01R 33/07* (2006.01)
*G01R 33/54* (2006.01)

(56) References Cited

U.S. PATENT DOCUMENTS

| | | | |
|---|---|---|---|
| 2003/0083588 A1* | 5/2003 | McClure | A61B 5/05 600/547 |
| 2010/0156421 A1* | 6/2010 | Sukkau | G01R 33/3415 324/318 |
| 2010/0176809 A1* | 7/2010 | Biber | G01R 33/3692 324/309 |
| 2010/0289492 A1 | 11/2010 | Biber et al. | |
| 2017/0248665 A1* | 8/2017 | Ludwig | A61B 5/05 600/547 |

* cited by examiner

DEVICE AND METHOD FOR POSITIONING IN A MAGNETIC FIELD OF A MAGNETIC RESONANCE TOMOGRAPHY SYSTEM USING MAGNETIC FIELD STRENGTH

The application claims the benefit of German Patent Application No. DE 10 2017 202 399.6, filed Feb. 15, 2017, which is hereby incorporated by reference in its entirety.

TECHNICAL FIELD

The disclosure relates to a method for positioning in a magnetic field of a magnetic resonance tomography system and a positioning device, wherein the positioning device may be moved along an axis, and a magnetic resonance tomography system with the positioning device.

BACKGROUND

Magnetic resonance tomography systems are imaging devices that, in order to depict an examination object, align nuclear spins of the examination object with a strong outer magnetic field and by way of a magnetic alternating field excite the same for precession about this alignment. The precession or return of the spins from this excited state into a state of less energy in turn generates a response in the form of a magnetic alternating field that is received by antennas.

With the aid of magnetic gradient fields, spatial encoding is impressed on the signals and this subsequently permits assignment of the received signal to a volume element. The received signal is then evaluated, and a three-dimensional imaging representation of the examination object is provided. The signal may be received using local antennas, so-called local coils, arranged directly on the examination object to achieve a better signal-noise ratio.

The resonance frequency of the nuclear spins, also called the Larmor frequency, is directly proportional to an outer static or quasi-static magnetic field including the static magnetic field B0 and the gradient fields. A magnetic resonance scan is possible in a region in which the static B0 magnetic field is sufficiently homogeneous. This region may be limited to a sphere with a diameter of a few tens of centimeters. To examine larger body regions, it is necessary to move these through the homogeneous magnetic field region, for example, on a patient bed.

It is, for example, known to provide patient beds with a cable pull that is connected to an encoder and supplies a signal as a function of the position of the patient bed. Such cable pulls may be associated with play, for example, on a change of direction. In addition, it is first of all necessary to establish a relationship between the encoder's position information and the magnetic field, which may possibly also change from examination to examination.

SUMMARY AND DESCRIPTION

Therefore, the object is to provide a device and an improved method for positioning in relation to the magnetic field.

The object is achieved by the positioning device for positioning in a static magnetic field of a magnetic resonance tomography system and by the magnetic resonance tomography system, the patient bed and the method for positioning.

The scope of the present disclosure is defined solely by the appended claims and is not affected to any degree by the statements within this description. The present embodiments may obviate one or more of the drawbacks or limitations in the related art.

The positioning device in a static magnetic field of a magnetic resonance tomography system may be moved along a first axis in the magnetic field. For example, the positioning device may be an electric, pneumatic, or hydraulic drive that moves the positioning device along a rail or comparable linear guide. For example, the positioning device and the linear drive may be part of a patient bed.

The positioning device includes a plurality of magnetic-field-strength sensors arranged at a distance from one another in the direction of the first axis in predetermined positions on the positioning device. Hall sensors are, for example, conceivable, but another possibility would be field probes based on electron or nuclear spin or devices based on an induction effect (e.g., a rotating coil or coils that use the movement of the bed relative to the magnetic field). Herein, the magnetic-field strength may relate to the value of the static magnetic field B0, for example, by a combination of several Hall sensors arranged in different, non-parallel planes so that the surface normals of the planes span a 3-dimensional space. However, it is also conceivable for the acquired magnetic-field strength to be the strength of a component in a predetermined direction. Herein, the direction may be defined by the arrangement of the magnetic-field-strength sensor on the positioning device, for example, the patient bed. The magnetic field sensors may be distributed over a substantial part of the extension of the positioning device along the first axis, for example, half or the entire length. Herein, the distribution may be equidistant so that the distances between the magnetic-field-strength sensors are identical.

The static magnetic field of a magnetic resonance tomography system is virtually homogeneous in a magnetic resonance scanning examination region while, outside or in the direction of the opening of the patient tunnel, for example, the static magnetic field varies greatly as a function of the position. A plurality of magnetic-field-strength sensors distributed on the positioning device along the direction of the first axis may advantageously provide that there is a magnetic-field-strength sensor in a region with a sufficiently high magnetic-field-strength gradient in order to determine the position with sufficient precision. Herein, in the case of a magnetic-field-strength sensor that acquires the value, advantageously the orientation of the sensor to the magnetic field is not important. On the other hand, a defined orientation of the magnetic field sensors on the positioning device enables the use of a simpler magnetic-field-strength sensor, which only acquires the magnetic-field strength of a component in a direction predetermined by orientation.

The patient bed includes a moving unit by which the patient bed may be moved along a plurality of axes in relation to the magnetic resonance tomography system. Here, it would be conceivable, for example, to use a crossbar system or a transport system in contact with the ground, such as swivel-mounted rollers or the like, or, for example, also a combination of a linear rail for the lying surface in one axis of motion and a ground transport system in a plurality of axes of motion.

Herein, the positioning device is designed to ascertain a position and/or location or orientation of the patient bed relative to the magnetic resonance tomography system. Details of how the relative position is ascertained are disclosed herein for the positioning device and the magnetic resonance tomography system.

The patient bed is designed to output a position-deviation signal as a function of the relative position determined and a predetermined setpoint position. Herein, the position-deviation signal may be a signal on a display for an operator.

The patient bed advantageously makes correct positioning on the magnetic resonance tomography system easier for the operator.

The method for calibrating a positioning device includes an act of acquiring a relative position of the positioning device in relation to the magnetic resonance tomography system by a facility for determining a relative position. The facility for determining a relative position may be arranged on the positioning device permanently or only for carrying out the method for calibration. This may be a mechanical, electrical, or optical sensor that supplies a position signal to the controller in one only or a plurality of predetermined relative positions. However, a continuous sensor, such as, for example, an encoder or a laser or an ultrasound length measuring system connected to a cable pull would also be conceivable.

In one act, the controller acquires a magnetic-field-strength measured value of a magnetic-field-strength sensor.

In a further act, the controller stores the magnetic-field-strength measured value and the relative position in the memory. Herein, it is also conceivable for the relative position to be encoded or stored by a specific choice of a memory cell for the magnetic-field-strength measured value, for example, in a table, or in some other way.

Advantageously, the method for calibration enables production tolerances, for example, for the magnetic-field-strength sensors and/or the magnet, to be acquired and taken into account during later positioning thus achieving higher precision during the positioning.

The method for positioning relates to positioning of a positioning device at a predetermined relative position in a magnetic resonance tomography system, wherein the magnetic resonance tomography system includes a controller, a memory, and a plurality of magnetic-field-strength measured values as a function of a plurality of relative positions is stored in the memory. Herein, the relative position may also be indicated by the memory location of the magnetic-field-strength measured value.

The method for positioning includes the act of selecting a magnetic-field-strength sensor from the plurality of magnetic-field-strength sensors and ascertaining a magnetic-field strength assigned to the predetermined relative position for the selected magnetic-field-strength sensor by the controller as a function of the relative positions and magnetic-field strength values stored in the memory. The controller may select a magnetic-field-strength sensor with a particularly high magnetic-field-strength gradient for the predetermined relative position. The controller may ascertain this, for example, from the stored magnetic-field-strength measured values and relative positions. However, it is also conceivable for an assignment of magnetic-field-strength sensors to regions of relative positions to have been stored in advance, for example, during the calibration. For example, the controller may ascertain the magnetic-field strength assigned to the relative position using magnetic-field strengths assigned in the memory to relative positions or regions of relative positions or also by linear interpolation or some other kind of interpolation of curves specified by value pairs for relative positions and magnetic-field strength in the memory. It is also conceivable for a function already to have been formed from the value pairs from the dependence of the magnetic-field strength on the relative position during the calibration so that the value pairs no longer have to be available during the actual positioning.

In one act of the method for positioning, the positioning device is moved along the first axis. For example, the controller may actuate a drive of the positioning device. Herein, the moving may take place from an initial position estimated using the stored measured values and relative positions or also starting from an end position. Also conceivable is a movement scheme according to an algorithm, (e.g., interval nesting), in order to make the positioning quicker or more precise.

In one act, a measured value of the magnetic-field-strength sensor ascertained is acquired. This may be performed by the controller during the movement or even with a stopped positioning device.

In one act of the method for positioning, the controller compares the acquired measured value with the magnetic-field strength ascertained.

In a further act of the method for positioning, the controller stops the positioning device when the acquired measured value matches the magnetic-field strength ascertained. Herein, matching may also be a deviation of the acquired measured value from the magnetic-field strength ascertained by less than 0.1%, less than 0.5%, less than 1%, less than 2%, or less than 5%.

In a further act, the controller continues with the act of moving the positioning device along the first axis when the acquired measured value does not match the magnetic-field strength ascertained.

The magnetic resonance tomography system shares the advantages of the positioning device.

In one conceivable embodiment of the positioning device, the first axis is substantially aligned parallel to the field direction of the static magnetic field. Substantially, the design may be such that the first axis and the field direction of the static magnetic field enclose an angle of less than 2 degrees, less than 5 degrees, or less than 10 degrees. Herein, the field direction of the static magnetic field refers to the field direction in an examination region with a homogeneous field strength, (which may also be referred to as the z-direction), and extends longitudinally through a patient opening of the superconducting field magnet. In the case of rotationally symmetrical field magnets around the patient opening, the z-direction is aligned parallel to the axis of symmetry of the rotational symmetry.

Advantageously, due to the symmetry properties, evaluation of measured magnetic field values is simpler with a movement along the Bz direction.

In one possible embodiment of the positioning device, the positioning device includes a position-determining facility for identifying a predetermined reference position of the positioning device in relation to the magnetic field. The position-identifying facility may be mechanical, electrical, or optical. Conceivable are buttons, cameras, or sensors, which acquire a marking with a predetermined reference position in relation to the magnetic field, (e.g., a pin or elevation), which actuate a button or an optical pattern, a reflector for a light barrier, or the like. Herein, it is also possible for a counterpart of this position-identifying facility to be arranged on the field magnet or magnetic resonance tomography system. With a characteristic magnetic field profile, also possible would be a special, characteristic magnetic-field strength that only occurs at a specific position and may be acquired by a calibrated magnetic-field-strength sensor, as described below. Herein, it is in principle possible for the roles of sensor and marking to be switched so that, for example, a sensor is arranged in a predetermined relative position to the magnetic field and a marking is moved relative thereto.

Advantageously, the positioning device may use the position-identifying facility to re-determine the zero point in order, for example, to take account of a newly positioned patient bed.

In one conceivable embodiment of the positioning device, at least one magnetic-field-strength sensor of the plurality of magnetic-field-strength sensors is a calibrated sensor for acquiring an absolute magnetic-field strength. In other words, the calibrated magnetic-field-strength sensor supplies a signal from which it is possible to determine an absolute value determined by physical units for the magnetic-field strength directly, e.g., using a predetermined proportionality constant.

Advantageously, the use of a calibrated magnetic-field-strength sensor enables the measurement of an absolute magnetic-field strength so that, in the case of a known magnetic field of the magnetic resonance tomography system, it is possible to dispense with a repeat calibration of the positioning device. Herein, it is conceivable for all magnetic-field-strength sensors of the device to be calibrated. However, it is also possible for only one of the magnetic-field-strength sensors to be calibrated and, with known distances of the magnetic field sensors and overlapping acquisition regions, for the other magnetic-field-strength sensors in each to be calibrated to one another by the controller. To this end, the calibrated magnetic-field-strength sensor is moved into a position in which it is still able to use the magnetic field to determine the position precisely and simultaneously a second, non-calibrated magnetic-field-strength sensor is in a region suitable for determining the position, in which, for example, the magnetic field gradient is sufficiently high and not equal to zero. As the distance is known, the position of the second magnetic-field-strength sensor is also known. The magnetic-field strength has already been determined for this position with the first calibrated magnetic-field-strength sensor. Hence, for this position, at which the second magnetic-field-strength sensor is now located, the magnetic-field strength and the precise location are known so that the second magnetic-field-strength sensor may be calibrated in that, for example, a proportionality factor is determined from the signal strength of the second magnetic-field-strength sensor and absolute magnetic-field strength by the formation of quotients. This calibration may be continued in the form of a chain for the other non-calibrated magnetic-field-strength sensors and so, for example, establish a length scale using the measured values of the individual magnetic-field-strength sensors over the entire length of a patient bed.

In one possible embodiment of the magnetic resonance tomography system, the position-determining facility and/or the magnetic resonance tomography system include an automatically acquirable reference mark and a marking sensor. The reference mark and the marking sensor form a mutually matched pair so that the marking sensor may acquire the reference mark. For example, the reference mark may be a mechanical elevation or indentation and the marking sensor a mechanical button or switch, which is actuated by the reference mark in a predetermined reference position. For example, optical patterns and a camera are also conceivable. The reference mark and the marking sensor may be moved by a moving unit of the positioning device along the first axis in relation to one another. They may both be provided on the positioning device, which is, for example, part of a patient bed, as long as this prespecifies a predetermined reference position in relation to the magnetic resonance tomography system and in particular to the static magnetic field, for example when the patient bed is a permanent component of the magnetic resonance tomography system. However, it is also conceivable for one of these two, reference mark or marking sensor, to be provided on the positioning device and the other to be arranged on the magnetic resonance tomography system with a fixed relationship to the magnetic field. The marking sensor is designed to output a reference signal in the case of a predetermined relative position to the reference mark.

Advantageously, the marking sensor and the reference mark provide a simple and inexpensive solution for establishing a spatial relationship and in this way, for example, with a separable patient bed, to provide a reference point on the length scale of the positioning device in relation to the magnetic resonance tomography system and the field magnet.

In one conceivable embodiment of the magnetic resonance tomography system, the magnetic resonance tomography system includes a controller and a memory. The controller is designed to move the positioning device along the first axis, to receive a signal with a magnetic-field strength from one of the magnetic-field-strength sensors and to compare it with a stored magnetic-field strength value. Herein, the stored magnetic-field strength value may have been taken from a table of positions and magnetic-field strength values or also ascertained by interpolation or by a function for a specific position.

Advantageously, the magnetic resonance tomography system may identify a specific position, which it achieves on the moving, by moving and comparing measured magnetic-field strength values with stored measured values.

In one possible embodiment of the magnetic resonance tomography system, the memory has stored magnetic-field strength values for different positions of the magnetic-field-strength sensor along the first axis. Also conceivable is an embodiment with which the magnetic-field strength values at different positions are stored in the form of a function or interpolation or calculation of the function is used to calculate a magnetic-field strength value for a predetermined position and then held in a memory or register for the comparison.

The magnetic-field strength values for different positions advantageously enable the compilation of a position grid and the identification of a position at several points on the first axis. Interpolation of magnetic-field strength values between the locations of the stored magnetic-field strength values even enables the provision of a continuous scale of the position along the first axis.

In one conceivable embodiment of the magnetic resonance tomography system, the magnetic resonance tomography system includes a facility for determining a position of the positioning device relative to the magnetic resonance tomography system along the first axis. For example, optical encoding and a corresponding sensor with a length scale are conceivable. Also conceivable are cable pulls with encoders or length measurement by sound or laser or other methods. Herein, the facility for determining the relative position may also be arranged detachably on the positioning device of the magnetic resonance tomography system. Herein, the controller is designed to move the positioning device along the first axis into different positions and to acquire measured values of the magnetic-field-strength sensor at the positions approached and, by the facility for determining a relative position, the respective position and store them in the memory. However, it would also be conceivable for the position and magnetic-field strength to be stored not directly, but as values derived therefrom, such as, for example, parameters of a fitting function.

The facility for determining a relative position advantageously enables the magnetic-field strength to be acquired as a function of the position at numerous positions along the first axis and hence to ascertain a table or function of the magnetic-field strength from the relative position to the magnet. This enables the positioning device to be calibrated and, on later use, the relative position to the magnet only determined with the positioning device without any additional, and possibly cost-driving, facility for determining a relative position.

In one possible embodiment of the patient bed, the patient bed is designed to control the moving unit as a function of the position-deviation signal such that the patient bed adopts the predetermined setpoint position. For example, the patient bed may include a motor control unit that generates control signals for motors of the moving unit from the position-deviation signal.

Advantageously, the bed is able to adopt a predetermined position on the magnetic resonance tomography system autonomously and hence facilitate the operator's work. This in particular avoids operator activities in the immediate vicinity of the strong magnetic fields.

In one possible embodiment of the method for calibration, the acts of the determination of a relative position of the positioning device in relation to the magnetic resonance tomography system, of the acquisition of a measured value of a magnetic-field-strength sensor and of the storage of the measured value and the relative position in the memory are repeated for a plurality of different relative positions.

Advantageously, in this way, the method for calibration also acquires deviations of the magnetic field at different locations along the first axis thus enabling individual deviations of individual devices to be taken into account and the measuring accuracy of the position to be increased.

In one conceivable embodiment of the method for calibration, the method is repeated for some or all of the plurality of magnetic-field-strength sensors.

The performance of calibration for some or all the magnetic-field-strength sensors enables the use of less expensive magnetic-field-strength sensors without impairing the measuring accuracy. Therefore, it is also conceivable for only one of the magnetic-field-strength sensors to be calibrated and then used as a reference for the calibration of further magnetic-field-strength sensors in that the uncalibrated magnetic-field-strength sensors are moved to the same position and the magnetic-field strength acquired there in advance with the calibrated magnetic-field-strength sensor is used as a reference.

In one conceivable embodiment of the method for calibration, a reference magnetic-field-strength value is stored in the memory. The stored reference magnetic-field-strength may be a characteristic magnetic-field strength value that, with a field magnet, only occurs in a narrowly limited space along the first axis and hence defines a position along the first axis. For example, along the axis of symmetry or Z-axis of a field magnet with a central patient tunnel, there is a steep drop in the magnetic field with values of between 80% and 20% of the magnetic-field strength B0 in the examination region, which may precisely define a position along the z-axis by a magnetic-field strength. In this embodiment of the method, furthermore the following subacts are carried out.

In one subact, the positioning device is moved along the first axis. Herein, the movement may take place in small acts corresponding to a measuring accuracy to be achieved later. However, also conceivable is movement in acts, which then decreases with the repetition disclosed below in the sense of interval nesting and converges toward a position corresponding to the stored reference magnetic-field-strength.

In a further subact, the magnetic-field-strength sensor acquires a measured value.

In another subact, the controller compares the acquired measured value with the stored reference magnetic-field-strength value.

In one subact, the controller stops the positioning device when the acquired measured value matches the stored reference magnetic-field-strength value. In this case, the reference position assigned to the stored reference magnetic-field-strength is reached.

In another subact, the controller continues the method with the subact of moving the positioning device when the acquired measured value does not match the stored reference magnetic-field-strength value. Herein, depending upon the embodiment, in the case of a linear search, the movement may be continued in the same direction. It is also conceivable for the direction of movement in the sense of interval nesting to change direction when the +/− sign of the difference between the reference magnetic-field-strength and the acquired magnetic-field strength formed by the controller has changed compared to a previous passage through the subacts of this embodiment of the method for calibration.

Advantageously, this enables a reference position assigned to the reference magnetic-field-strength to be determined quickly and reliably.

In one possible embodiment of the method for positioning a positioning device, the method has the act of the determination of a magnetic-field-strength sensor from the plurality of magnetic-field-strength sensors by the controller. In addition, the controller ascertains a magnetic-field strength assigned to the predetermined relative position as a function of relative positions and magnetic-field strength values stored in the memory.

In one act, the controller moves the positioning device along the first axis. This may take place as described above for the calibration for example in one direction with a linear search or, for example, in alternating directions with interval nesting.

In another act, the controller acquires a measured value of the magnetic-field-strength sensor.

In a further act, the controller compares the acquired measured value with the magnetic-field strength ascertained.

In one act, the controller stops the positioning device when the acquired measured value matches the magnetic-field strength ascertained.

In another act, the controller continues the method for positioning with subact of the method when the acquired measured value does not match the magnetic-field strength ascertained. As described above for the calibration, herein, the direction of movement of the moving may also change as a function of the acquired magnetic-field-strength measured value.

BRIEF DESCRIPTION OF THE DRAWINGS

The above-described properties, features and advantages of this disclosure and also the manner with which these are achieved will become clearer and more plainly comprehensible in conjunction with the following description of the exemplary embodiments explained in more detail in conjunction with the drawing, in which.

DETAILED DESCRIPTION

Figure 1:
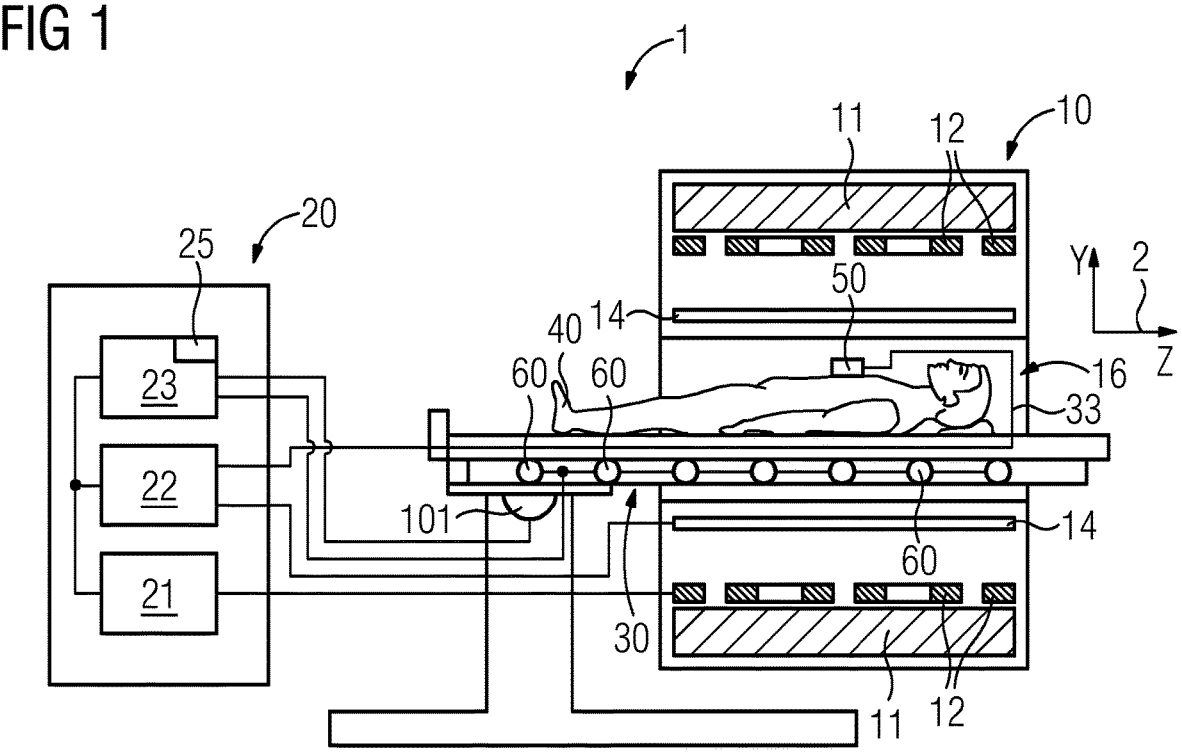
FIG. 1 depicts an exemplary schematic representation of a magnetic resonance tomography system with a positioning device.

FIG. 1 depicts a schematic representation of an embodiment of a magnetic resonance tomography system 1 with a positioning device 100, which is embodied here by way of example as part of a patient bed 30.

The magnet unit 10 includes a field magnet 11 that generates a static magnetic field B0 for the alignment of nuclear spins in specimens or patients 40 in a receiving region. The receiving region is arranged in a patient tunnel 16 extending in a longitudinal direction 2 through the magnet unit 10. The field magnet 11 may be a superconducting magnet able to provide magnetic fields with a flux density of up to 3T or even more with the most recent devices. However, it is also possible to use permanent magnets or electromagnets with normally conducting coils for lower field strengths.

The magnet unit 10 also includes gradient coils 12 designed for the spatial differentiation of the acquired image regions in the examination volume to superimpose the magnetic field B0 with variable magnetic fields in three spatial directions. The gradient coils 12 may be coils made of normally conducting wires able to generate fields that are orthogonal to one another in the examination volume.

The magnet unit 10 also includes a body coil 14 designed to emit a radio-frequency signal supplied via a signal line 33 into the examination volume and to receive resonance signals emitted by the patient 40 and supply them via a signal line. The body coil 14 for emission of the radio-frequency signal and/or the reception may be replaced by local coils 50 arranged in the patient tunnel 16 close to the patient 40. However, it is also conceivable for the local coil 50 to be designed for transmission and reception and therefore for a body coil 14 to be dispensed with.

A control unit 20 supplies the magnet unit 10 with the different signals for the gradient coils 12 and the body coil 14 and evaluates the received signals.

For example, the control unit 20 includes a gradient activation system 21 designed to supply the gradient coils 12 via leads with variable currents that provide the desired gradients fields in the examination volume in temporal coordination.

The control unit 20 also includes a radio-frequency unit 22 designed to generate a radio-frequency pulse with a specified temporal course, amplitude, and spectral power distribution to excite a magnetic resonance of the nuclear spins in the patient 40. Herein, it is possible to achieve pulse power in the kilowatt range.

Figure 4:
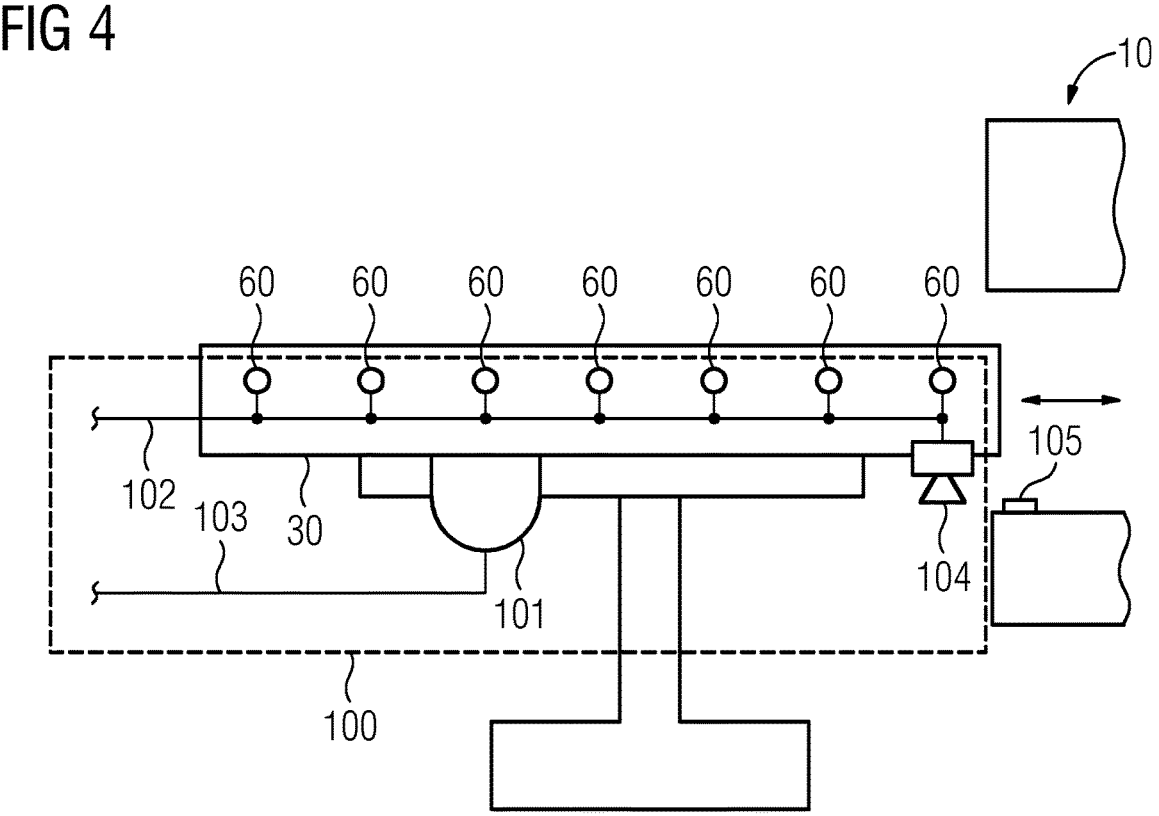
FIG. 4 depicts an example of a patient bed with a positioning device.

The magnetic resonance tomography system 1 further includes a positioning device 100, in the exemplary embodiment depicted part of the patient bed 30. However, also conceivable is a positioning device, which may be arranged wholly or partially temporarily on the patient bed. Details of the positioning device 100 are depicted in FIG. 4.

Figure 2:
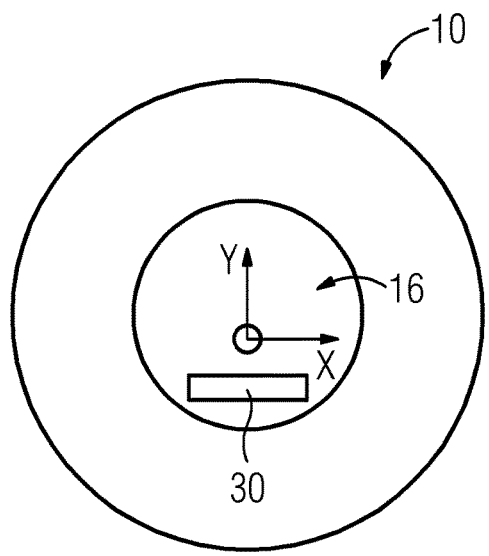
FIG. 2 depicts an exemplary schematic cross section through a field magnet of a magnetic resonance tomography system.

FIG. 1 also depicts the coordinate axes to be used below wherein the designations x, y, and z are selected arbitrarily. The z-coordinate axis extends centrally through the patient tunnel 16 and simultaneously indicates an axis of symmetry for the magnet unit 10 and the field magnet 11, which, as is evident in the cross section in FIG. 2, has an approximately cylindrical shape, which is symmetrical to an axis of rotation in the center point. The y-coordinate axis is arranged perpendicular to the z-axis and vertically upward in the drawing plane in FIG. 1. The x-coordinate axis is only shown in the cross section in FIG. 2 and is again arranged perpendicular to both the z-coordinate axis and the y-coordinate axis. As a result of the rotational symmetry of the field magnet 11, it is possible for the x-y-coordinate axes to be rotated as desired about the z-coordinate axis without the following description changing. Herein, the first axis identified below is aligned substantially parallel to the z-axis, e.g., it encloses an angle smaller than 20 degrees, smaller than 10 degrees, smaller than 5 degrees, or smaller than 1 degree with the z-axis.

Figure 3:
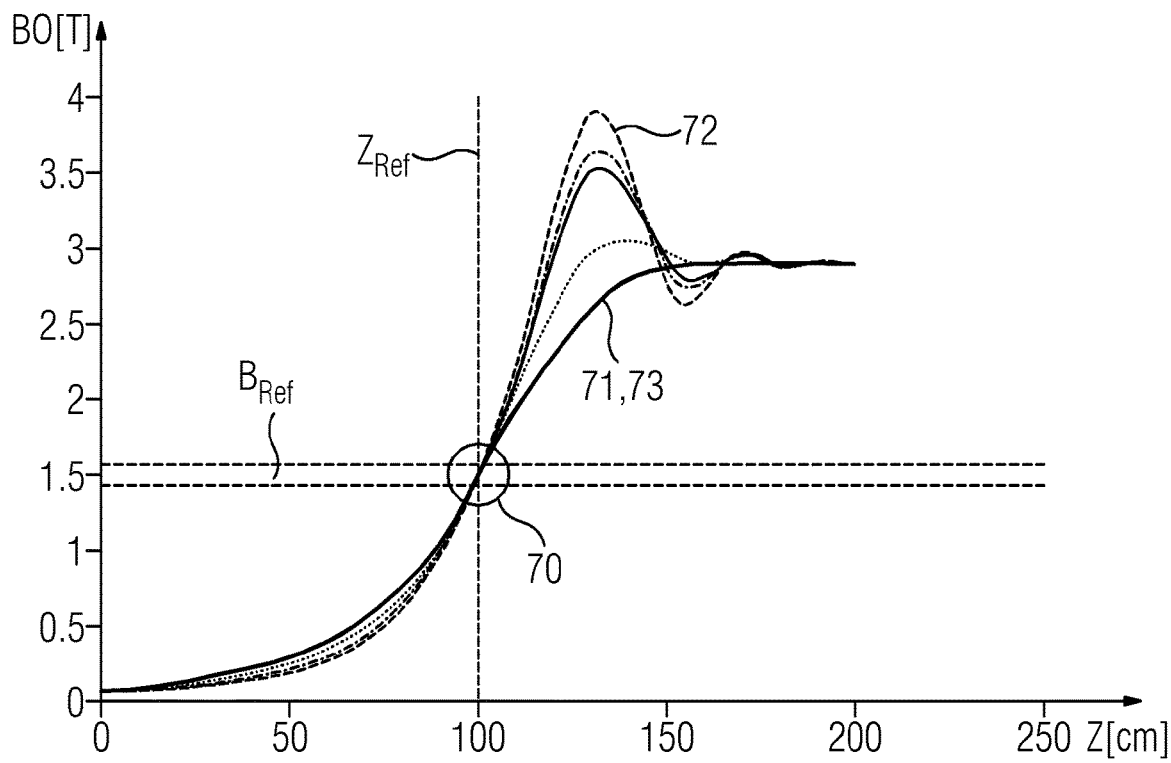
FIG. 3 depicts an exemplary representation of functions of the magnetic-field strength of a field magnet as a function of the z-coordinate for different x-y-coordinates.

FIG. 3 depicts profiles of the magnetic-field strength B0 measured by a magnetic-field-strength sensor 60 as a function of the z-coordinate. The zero point is 200 cm before the isocenter of the B0 field magnet on the z-coordinate axis. Curves with different x-y-coordinates or distance to the z-coordinate axis are shown. Such curves of the B0-field magnet are measured in that the magnetic-field-strength sensor 60 is moved through the B0 field with the same orientation and a fixed x-y-coordinate along the z-coordinate axis and herein the measured values for magnetic-field strength and z are acquired.

Herein, the curve 71 is assigned to a magnetic-field-strength sensor directly on the z-coordinate axis (x=0, y=0), while the curve 72 corresponds to a profile with the greatest distance to the z-coordinate axis. Herein, in a first region around $Z_{REF}$ of approximately ±20 cm, it is characteristic that all curves have a steep monotonic rise that enables unique and relatively precise determination of the position using the magnetic field. Herein, a steep rise can be considered to be, for example, a rise value of greater than $0.2*B0_{iso}$ divided by the length of the B0 field magnet in the z-direction. As a result of the steep rise, even with a faulty measurement of the magnetic-field strength, indicated by the horizontal bar 73 around the value $B_{ref}$, the reference z-coordinate $z_{ref}$ may be determined with high precision, as indicated by the narrow vertical bar 74.

In one embodiment, the present disclosure further exploits the knowledge that the curves for numerous x-y-coordinates intersect one another or approach one another with different distances to the z-coordinate axis in an intersection region 70. The intersection region 70 is located at a value $B_{ref}$ of the magnetic-field strength, which for the 3T magnet depicted is at approximately 50% of the magnetic-field strength $B0_{iso}$ in the isocenter. This may vary, for example, the value may be within an interval of between 20% and 80% of the magnetic-field strength in the isocenter. Using this value, a first magnetic-field-strength sensor 60, which is calibrated in the sense that a predetermined output signal level corresponds to a predetermined magnetic-field strength, is able to determine a reference point relative to the field magnet and the isocenter thereof for positioning along the first axis solely using the magnetic field.

FIG. 4 is a schematic representation of a positioning device 100 as part a patient bed 30. In the embodiment in FIG. 4, the controller 23 and the memory 25 of the positioning device 100 are provided by the controller 23 of the magnetic resonance tomography system 1, as depicted in FIG. 1. However, it is also conceivable for the positioning device 100 to include a separate controller and memory so that, for example, the controller 23 of the magnetic resonance tomography system only transmits a command for calibrating or positioning at a communicated position to the controller of the positioning device 100 via a signal link and the positioning device 100 carries out the method autonomously by the separate controller.

A plurality of magnetic-field-strength sensors 60 are arranged at a distance from one another along the patient bed 30. The magnetic-field-strength sensors 60 may be distributed along the entire length of the patient bed 30 in the direction of the first axis, wherein equidistant distribution simplifies positioning, although this is not mandatory. The distance between the magnetic-field-strength sensors 60 may be such that in each case one of the magnetic-field-strength sensors 60 is also located in the first region of the magnetic field according to FIG. 3 around $Z_{REF}$ in which the magnetic-field strength rises steeply. Therefore, in the embodiment in FIG. 3, the maximum distance between the magnetic-field-strength sensors 60 would be 40 cm. This also enables sufficiently precise positioning to be achieved.

Conceivable magnetic-field-strength sensors 60 are, for example, Hall sensors. With these, the output signal is not dependent solely upon the magnetic-field strength, but also on an angle of the semiconductor element in the Hall sensor with respect to the magnetic field vector. A maximum signal is obtained when the magnetic field vector is aligned parallel to a surface normal of the flat Hall element, perpendicular to the current direction and line connecting the Hall contacts. Therefore, the surface normals of the magnetic field sensors 60 may be aligned substantially parallel to the z-direction, which, as depicted in FIG. 3 may be the magnetic field component.

Also conceivable are magnetic-field-strength sensors 60 based on other physical principles, for example rotating induction coils or YIG field cameras. It is also possible for a plurality of Hall sensors with preferential directions spanning a three-dimensional space to determine an amount of the magnetic field vector and hence for the absolute magnetic-field strength to be determined by the magnetic-field-strength sensor 60. Then, precise alignment of the magnetic-field-strength sensors 60 is not necessary.

For moving the positioning device 100 relative to the magnet unit 1, the magnet unit includes a moving unit 101, which is arranged on the patient bed 30 and is able to move the patient bed with the magnetic-field-strength sensors 60 along the first axis, here the z-axis, in both units controlled by the controller 23.

The positioning device 100 also includes a position-determining device 104. This may be provided permanently or may also only be arranged on the positioning device 100 for carrying out the method for calibration. The position-determining device 104 is designed to identify a predetermined relative position of the positioning device 100 to the magnet unit 10. For example, it is conceivable for a camera to be arranged on the positioning device 100 as the position-determining device 104, wherein the camera is aligned such that, on a movement of the positioning device 100 along the first axis, it passes by a marking 105 arranged on the magnet unit 10. If the camera identifies the pattern in a predetermined location, this may characterize the predetermined relative position, which the controller 23 then identifies by the camera. However, other position-determining devices 104 are conceivable, for example, light barriers or scanners or also simple buttons on the positioning device 100 that are actuated by an elevation on the magnet unit 10. However, it is also conceivable to move the marking 105 relative to a position-determining device 104, wherein the position-determining device 104 is arranged in a predetermined fixed position relative to the magnetic field $B0_{iso}$.

It is furthermore also conceivable in one embodiment for the positioning device 100 to be part of a patient bed 30 and for the moving unit 36 of the patient bed 100 to be not only capable of displacing the lying surface along the z-axis but also to move the entire patient bed 30 three-dimensionally. For example, a roller system may be provided in the foot of the patient bed 30 to permit free three-dimensional positioning. Herein, the roller system may have a drive and a motor control unit so that the positioning may also take place automatically. Herein, the magnetic-field-strength sensors 60 may enable the positioning device 100 also to determine the three-dimensional position at a greater distance from the magnetic resonance tomography system 1 due to the stray field. To this end, it is conceivable for the positioning device 100 to store a predetermined magnetic field map or, for example, by a calibration process by three-dimensional movement on predetermined positions or paths and recording the signals of the magnetic-field-strength sensors 60, to compile a map itself.

A comparison of current measured values of the magnetic-field-strength sensors 60 in the controller 23, possibly using interpolation and/or an error-minimization method, enables the current position of the patient bed 30 to be determined. The provision of a plurality of magnetic-field-strength sensors with a known relative position to one another also enables unambiguous determination of the position including the orientation of the patient bed 30 to the magnetic resonance tomography system 1. If a predetermined setpoint position is approached, the difference vector may be used to determine a direction and activate the moving unit 36 accordingly by a motor control unit.

Figure 5:
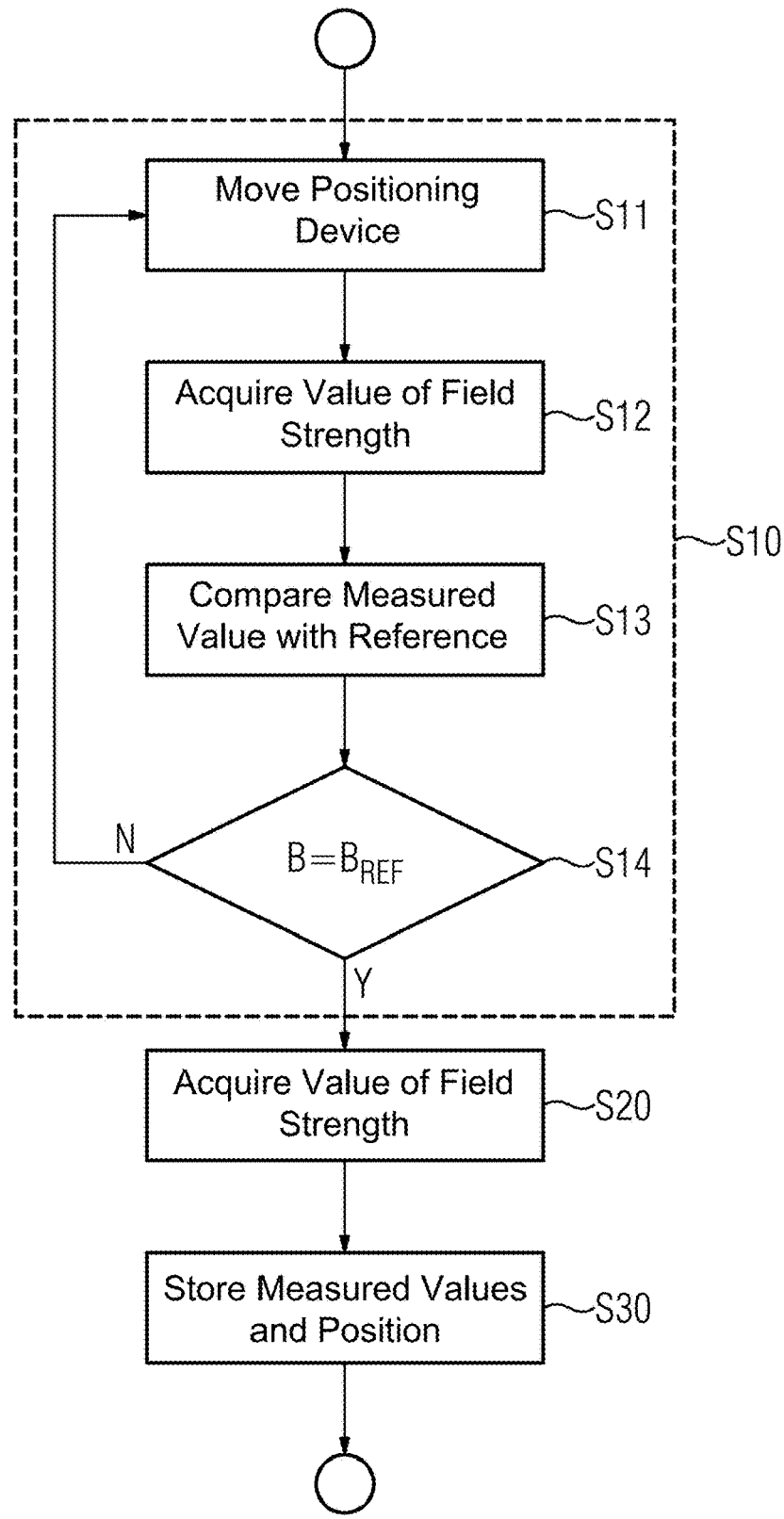
FIG. 5 depicts a schematic flow diagram of a method for calibrating a positioning device.

FIG. 5 is a schematic representation of a flow diagram for a method for the calibration of a positioning device.

In act S10, a relative position of the positioning device 100 in relation to the magnetic resonance tomography system is determined by the position-determining device 104.

This act is carried out differently depending upon the embodiment of the position-determining device. For example, the position-determining device 104 may be a camera, light barrier or scanner or the like that is able to identify or acquire a marking 105. The controller 23 then actuates the moving unit 101 until the position-determining device 104 identifies the marking 105. Because the marking 105 is arranged in a predetermined position with reference to the magnetic field unit 10 and the isocenter of the field magnet 11, the position-determining device 104 and the positioning device 100 connected thereto are then also in a predetermined relative position to the magnetic field and the magnet unit 10. The controller may then, for example, stop the moving unit 101. However, it is also conceivable for the following acts to be carried out quickly enough for them to take place during movement without falsifying acquired measured values so that no stop is necessary. To find the marking, it may also be necessary for the controller 23 to change the direction of movement by the moving unit 101.

In act S20 of the method for calibration, a measured value of a magnetic-field-strength sensor is acquired by the controller 23. This may entail a magnetic-field-strength sensor 60 that at this time is located in the region of the steep rise in the magnetic-field strength as a function of the position along the first axis, as already explained in connection with FIG. 3. However, it is also conceivable for reasons of redundancy for the controller 23 also to acquire the measured values of other magnetic-field-strength sensors 60 in order subsequently to increase the precision by correlation of the measured values of a plurality of sensors or, in the case of profiles of the magnetic-field strength that do not rise or fall in a steeply monotonic manner as a function of the position along the first axis, to enable an unambiguous determination of the position.

In another act S30 of the method for calibration, the measured value or measured values and the relative position are stored in the memory. Herein, for different magnetic-field-strength sensors 60, the predetermined relative position may be used to refer the position to a common reference point before storage or only after reading-out.

If the profile of the magnetic-field strength as a function of the position along the first axis is already known, for example, because, for a specific type of field magnet, the profile is reproduced in the prepared copies with sufficient precision, the value pair determined in act S20 may be used to calibrate the magnetic-field-strength sensor 60 to the curve and then for position determination by the calibrated magnetic-field-strength sensor.

In one possible embodiment of the method for calibration, the acts S10 to S30 are repeated for a plurality of different relative positions.

Herein, it is on the one hand conceivable for the position-determining facility 104 to mark a plurality of predetermined positions, for example by different optical or mechanical markings. It is then possible, for one or more magnetic-field-strength sensors 60, for a plurality of value pairs of magnetic-field strength and relative position to be acquired by the controller 23 and stored in the memory 25. The magnetic resonance tomography system 1 is then able to acquire a profile of the magnetic-field strength along the first axis itself and hence calibrate its length scale including the magnetic-field-strength sensors 60. Intermediate values may be ascertained by interpolation.

In one conceivable embodiment of the method for calibration, the method is repeated for some or all of the plurality of magnetic-field-strength sensors 60.

Because the magnetic-field-strength profile only rises steeply monotonically in a restricted region around $Z_{REF}$, it is necessary, for position determination over a larger region, to use different magnetic-field-strength sensors. In order to calibrate all these sensors, the method for calibration may be continued in each case in the form of a chain from one magnetic-field-strength sensor to the next, starting from the precalibrated magnetic-field-strength sensor 60 or the magnetic-field-strength sensor, which was arranged at the predetermined relative position the first time the act S10 was carried out in the region around $Z_{REF}$. To this end, it is only necessary for two adjacent magnetic-field-strength sensors to be simultaneously located in the steeply rising region around $Z_{REF}$. Herein, "rising" may be considered to be equivalent to "falling", because the two designations are interchangeable depending upon the alignment of the coordinate axis or even the side of the patient tunnel 16.

However, it is also possible for a magnetic-field-strength sensor 60 to be factory calibrated so that the output signal of the magnetic-field-strength sensor 60 enables this itself to be used as a position-determining facility 104 in that a predetermined output signal of the calibrated magnetic-field-strength sensor 60 specifies the predetermined relative position.

In this embodiment of the method for calibration, a reference magnetic-field-strength value is stored in the memory and in the act S10, the following subacts are performed subsequently.

In act S11, the positioning device 100 is moved along the first axis.

In act S12, a measured value of the magnetic-field-strength sensor 60 is acquired by the controller 23.

In act S13, the controller 23 compares the acquired measured value with the stored reference magnetic-field-strength value.

In act S14, the controller 23 stops the positioning device 104 when the acquired measured value matches the stored reference magnetic-field-strength value. Otherwise, the controller 23 continues the method for calibration with a jump to subact S11 when the acquired measured value does not match the stored reference magnetic-field-strength value.

Hence, it is also possible for a factory calibrated magnetic-field-strength sensor 60 with a known magnetic field profile for the field magnet 11 in this way to enable calibration of the other, uncalibrated, magnetic-field-strength sensors. To this end, a predetermined relative position is prespecified by a predetermined magnetic-field strength value and approached by the precalibrated magnetic-field-strength sensor 60 and then a measured value of the magnetic-field strength acquired and stored for positions of the other magnetic-field-strength sensors known from the predetermined distance between the magnetic-field-strength sensors.

Figure 6:
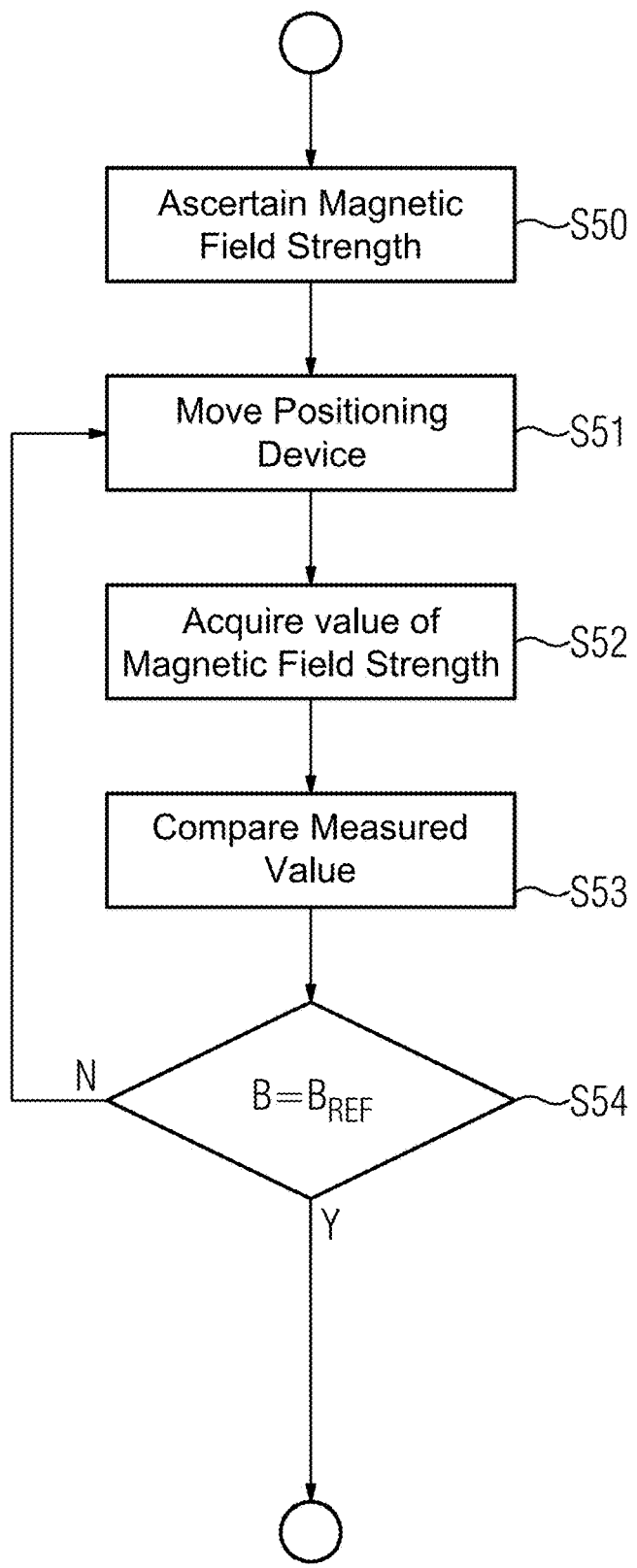
FIG. 6 depicts an exemplary schematic flow diagram of a method for positioning.

FIG. 6 is a schematic representation of a flow diagram of an embodiment of a method for positioning.

The method for positioning requires value pairs for the magnetic-field strength as a function of the position for the plurality of magnetic-field-strength sensors 60 along the first axis to be already ascertained and stored in the memory 25 of the controller 23. This may take place with the depicted method for calibration.

The method for positioning the positioning device 100 at a predetermined relative position has the act S50 of ascertaining a magnetic-field-strength sensor 60 from the plurality of magnetic-field-strength sensors 60 and ascertaining a magnetic-field strength assigned to the predetermined relative position by the controller as a function of the magnetic-field-strength sensor determined and relative positions and magnetic-field-strength values stored in the memory. Herein, the controller 23 may ascertain the magnetic-field-strength sensor 60, which, for the predetermined relative position of the positioning device 100, lies in the region of the steep rise in the magnetic-field strength around $Z_{REF}$ already explained with reference to FIG. 3. However, it would also be conceivable for another magnetic-field-strength sensor 60 to be selected. However, herein the precision of the positioning may be lower. However, it is also possible for a plurality of magnetic-field-strength sensors 60 to be selected and associated magnetic-field strength values ascertained thus enabling the subsequent performance of error minimization.

In act S51, the controller 23 moves the positioning device 100 along the first axis and, in act S52, acquires a measured value of the magnetic-field-strength sensor 60 determined. Herein, the method and acquisition may be performed simultaneously or in alternation. The controller 23 may determine the direction of the method for example from a gradient of the magnetic-field-strength curve and the difference between the already acquired magnetic-field strength and the value ascertained.

In act S53, the controller 23 compares the acquired measured value with the magnetic-field strength ascertained. Herein, it is also conceivable in the case of a plurality of determined magnetic-field-strength sensors for the controller 23 to perform an error-minimization method (for example, LSR) as a comparison and to evaluate minimum errors as a match.

In act S54, the controller 23 stops the positioning device 100 when the acquired measured value matches the magnetic-field strength ascertained or continues the method for positioning with subact S51 when the acquired measured value does not match the magnetic-field strength ascertained.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A positioning device for positioning in a static magnetic field of a magnetic resonance tomography system, the positioning device comprising:
   a plurality of calibrated magnetic-field-strength sensors arranged at a distance from one another in a direction of a first axis in the magnetic field in predetermined positions on the positioning device,
   wherein the positioning device is configured to move along the first axis in the magnetic field, and
   wherein the plurality of calibrated magnetic-field-strength sensors is configured to provide an absolute magnetic-field strength.

2. The positioning device of claim 1, wherein the first axis is substantially aligned parallel to a field direction of the static magnetic field.

3. The positioning device of claim 1, further comprising:
   a position-determining facility configured to identify a predetermined reference position of the positioning device in relation to the magnetic field.

4. A magnetic resonance tomography system comprising:
   a positioning device configured to be positioned in a static magnetic field of the magnetic resonance tomography system, wherein the positioning device comprises:
   a plurality of calibrated magnetic-field-strength sensors arranged at a distance from one another in a direction of a first axis in the magnetic field in predetermined positions on the positioning device,
   wherein the positioning device is configured to move along the first axis in the magnetic field, and
   wherein the plurality of calibrated magnetic-field-strength sensors is configured to provide an absolute magnetic-field strength.

5. The magnetic resonance tomography system of claim 4, wherein the positioning device further comprises a position-determining facility configured to identify a predetermined reference position of the positioning device in relation to the magnetic field,
   wherein the position-determining facility comprises an automatically acquirable reference mark and a marking sensor,
   wherein the reference mark and the marking sensor are configured to be moved along the first axis in relation to one another by the positioning device, and
   wherein the marking sensor is designed to output a reference signal at a predetermined relative position to the reference mark.

6. The magnetic resonance tomography system of claim 4, further comprising:
   a controller; and
   a memory,
   wherein the controller is configured to move the positioning device along the first axis to receive a signal with a magnetic-field strength from a calibrated magnetic-field-strength sensor of the plurality of calibrated magnetic-field-strength sensors and compare the received signal with a stored magnetic-field strength value.

7. The magnetic resonance tomography system of claim 6, wherein the memory has stored magnetic-field strength values for different positions of the calibrated magnetic-field-strength sensor along the first axis.

8. The magnetic resonance tomography system of claim 6, further comprising:
   a position-determining device configured to determine a position of the positioning device relative to the magnetic resonance tomography system along the first axis,
   wherein the controller is configured to move the positioning device along the first axis into different positions and to acquire measured values of the calibrated magnetic-field-strength sensor at the positions approached and, by the position-determining device, the respective position and store the measured values in the memory.

9. A patient bed comprising:
   a positioning device configured to be positioned in a static magnetic field of a magnetic resonance tomography system, wherein the positioning device comprises a plurality of calibrated magnetic-field-strength sensors arranged at a distance from one another in a direction of a first axis in the magnetic field in predetermined positions on the positioning device, wherein the positioning device is configured to move along the first axis in the magnetic field; and
   a moving unit by which the patient bed is configured to move along a plurality of axes in relation to the magnetic resonance tomography system,
   wherein the positioning device is configured to determine a position, an orientation, or both the position and the orientation of the patient bed relative to the magnetic resonance tomography system and to output a position-deviation signal as a function of the relative position determined and a predetermined setpoint position, and
   wherein the plurality of calibrated magnetic-field-strength sensors is configured to provide an absolute magnetic-field strength.

10. The patient bed of claim 9, wherein the patient bed is configured to control the moving unit as a function of the position-deviation signal such that the patient bed adopts the predetermined setpoint position.

11. A method for calibration of a positioning device of a magnetic resonance tomography system, the method comprising:

determining, by a position-determining device of the magnetic resonance tomography system, a relative position of the positioning device in relation to the magnetic resonance tomography system, wherein the position-determining device includes a plurality of magnetic-field-strength sensors;

acquiring, by a controller of the magnetic resonance tomography system, a measured value of the magnetic-field-strength sensor, wherein the measured value provides an absolute magnetic-field strength; and storing the measured value and the relative position in a memory of the magnetic resonance tomography system.

12. A method for calibration of claim 11, wherein the determining, the acquiring, and the storing are repeated for a plurality of different relative positions.

13. A method for calibration of claim 12, wherein the method for some or all of the plurality of magnetic-field-strength sensors is repeated.

14. The method for calibration of claim 11, wherein a reference magnetic-field-strength value is stored in the memory and in the determining of the relative position further comprises:

moving the positioning device along a first axis;

acquiring a measured value of the magnetic-field-strength sensor;

comparing the acquired measured value with the stored reference magnetic-field-strength value; and stopping the positioning device when the acquired measured value matches the stored reference magnetic-field-strength value or repeating the moving, the acquiring, and the comparing when the acquired measured value does not match the stored reference magnetic-field-strength value.

15. A method for positioning a positioning device at a predetermined relative position with a magnetic resonance tomography system, the method comprising:

determining, by a controller of the magnetic resonance tomography system, a calibrated magnetic-field-strength sensor from a plurality of calibrated magnetic-field-strength sensors;

ascertaining, by the controller, a magnetic-field strength assigned to the predetermined relative position as a function of the determined calibrated magnetic-field-strength sensor and the relative positions and magnetic-field strength values stored in a memory of the magnetic resonance tomography system, wherein the magnetic-field-strength values indicate an absolute magnetic-field strength;

moving the positioning device along a first axis;

acquiring a measured value of the determined calibrated magnetic-field-strength sensor;

comparing the acquired measured value with the ascertained magnetic-field strength; and stopping the positioning device when the acquired measured value matches the ascertained magnetic-field strength or repeating the moving, the acquiring, and the comparing when the acquired measured value does not match the ascertained magnetic-field strength.

* * * * *